US005763495A

United States Patent [19]

Magin et al.

[11] Patent Number: 5,763,495
[45] Date of Patent: Jun. 9, 1998

[54] WIDELY-BRIDGED ALCOHOL POLYETHOXYLATES AND THEIR USE

[75] Inventors: Ralph W. Magin; Joe D. Sauer, both of Baton Rouge, La.

[73] Assignee: Albemarle Corporation, Richmond, Va.

[21] Appl. No.: 720,596

[22] Filed: Sep. 30, 1996

[51] Int. Cl.$^6$ .................. A01N 33/08; C07C 217/42; C07C 217/50
[52] U.S. Cl. .................. 514/668; 424/406; 424/407; 424/408; 424/409; 504/127; 504/206; 564/505
[58] Field of Search .................. 564/505; 514/668; 504/127, 206; 424/406, 407, 408, 409

[56] References Cited

U.S. PATENT DOCUMENTS

| | | | |
|---|---|---|---|
| 3,331,892 | 7/1967 | Cyba | 260/920 |
| 3,371,039 | 2/1968 | Cyba | 252/32.7 |
| 3,992,349 | 11/1976 | Sparks | 260/32.6 R |
| 4,024,324 | 5/1977 | Sparks | 526/2 |
| 4,217,914 | 8/1980 | Jacquet et al. | 132/7 |
| 4,422,853 | 12/1983 | Jacquet et al. | 8/406 |
| 4,891,160 | 1/1990 | Vander Meer | 252/545 |
| 5,332,714 | 7/1994 | Albrecht et al. | 504/116 |
| 5,389,598 | 2/1995 | Berk et al. | 504/206 |
| 5,504,054 | 4/1996 | Murphy | 504/116 |

FOREIGN PATENT DOCUMENTS

| | | |
|---|---|---|
| 1369247 | 10/1974 | United Kingdom . |
| 1369248 | 10/1974 | United Kingdom . |
| 1369249 | 10/1974 | United Kingdom . |
| 1369250 | 10/1974 | United Kingdom . |
| 1513671 | 6/1978 | United Kingdom . |

OTHER PUBLICATIONS

Ida et al., JP 06240299 (8–1994) cited in Chem. Abst.: 122:191069, 1994.

Sparks, U.S. Published Patent Application B 596,692, published Feb. 17, 1976.

Voelkel et al., Journal of Chromatography, vol. 454, pp. 51–63 (1988).

*Primary Examiner*—Peter O'Sullivan
*Attorney, Agent, or Firm*—Philip M. Pippenger

[57] ABSTRACT

Described are $\omega,\omega'$-[$\alpha,\omega$-alkanediylbis(alkylimino)]bis (alkanolpolyethoxylates) in which (i) the alkane group has in the range of 4 to 12 carbon atoms, (ii) the alkyl groups can be the same or different and contain up to about 24 carbon atoms each, and (iii) the number of ethyleneoxy groups in each polyethoxylate group is in the range of 2 to about 50. These compounds are effective adjuvants for use with pesticides, especially herbicides and plant growth regulants, such as glyphosate.

13 Claims, No Drawings

5,763,495

1

WIDELY-BRIDGED ALCOHOL POLYETHOXYLATES AND THEIR USE

TECHNICAL FIELD

This invention relates to novel bridged alcohol polyethoxylates, the synthesis of such compounds and their use as adjuvants for pesticides, especially as adjuvants for use with herbicides and plant growth regulants.

SUMMARY OF THE INVENTION

Provided by this invention is a novel group of highly useful bridged alcohol polyethoxylates which are widely bridged, i.e., a pair of alcohol polyethoxylate moieties are bridged by a chain of carbon atoms that is at least four carbons in length. In particular, this invention provides in one of its embodiments, N,N'-alkylenebis (alkyliminoalkyleneoxyethoxylates) in which (i) the alkylene group has in the range of 4 to 12 carbon atoms and is at least 4 carbon atoms in length, (ii) the two alkylimino groups can be the same or different and contain up to about 24 carbon atoms each, (iii) the two alkyleneoxy groups can be the same or different and contain in the range of from 2 to about 6 carbon atoms each, and (iv) the number of ethyleneoxy groups in each of the two ethoxylate moieties is in the range of up to about 50. These compounds may be depicted by the formula:

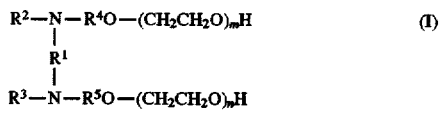

where $R^1$ is a straight or branched chain alkylene group that has in the range of 4 to about 12 carbon atoms and is at least 4 carbon atoms in length, $R^2$ and $R^3$ can be the same or different and are alkyl groups which contain up to about 24 carbon atoms each, $R^4$ and $R^5$ can be the same or different and are alkylene groups which contain in the range of from 2 to about 6 carbon atoms each, and n and m are the same or different numerals of in the range of 2 to about 50 each. While individual compounds of this invention can be isolated by careful separation techniques, the compounds of this invention are often mixtures in which n and m represent average numbers. Preferably, $R^1$ is a straight chain alkylene group, and it is also preferred that $R^1$ have in the range of 6 to about 12 carbon atoms. It is preferred that $R^2$ and $R^3$ be the same alkyl groups, and it is also preferred that each of $R^2$ and $R^3$ contain in the range of 6 to about 18 carbon atoms. Preferably $R^4$ and $R^5$ are the same alkylene groups, and it is also preferred that each of $R^4$ and $R^5$ contain in the range of 2 to about 4 carbon atoms.

The numerals n and m when in a mixture of compounds of the above formula represent average numbers of up to about 50, and preferably, whether in a single compound of the invention (where m and n are whole numbers) or in a mixture of compounds of the invention (where m and n are whole or fractional numbers), m and n are in the range of about 4 to about 25, and more preferably in the range of about 10 to about 20.

The compounds of this invention possess desirable properties rendering them suitable for use as adjuvants for increasing the usefulness and/or effectiveness of pesticides, especially pesticides used in connection with agriculture and rearing of livestock, such as, for example, herbicides, plant growth regulants, insecticides, miticides, fungicides, and biocides. The compounds of this invention are deemed of particular utility in enhancing the usefulness and effectiveness of herbicides and plant growth regulants, especially the usefulness and effectiveness of glyphosate (N-(phosphonomethyl)glycine), a well-known widely used herbicide generally employed in the form of an agriculturally acceptable salt. Among the advantages of use of the compounds of the present invention as such adjuvants are that it is possible to achieve enhanced phytotoxic and plant growth regulant effectiveness in an aqueous solution formed from as few as two added ingredients, such as a glyphosate salt and a compound of this invention. Secondly, it is possible pursuant to this invention to employ the glyphosate herbicide in dosage levels lower than currently recommended. Moreover, the formulation requires no polyvalent metal or metalloid components in its formation. Indeed, the preferred compositions are devoid of metal and metalloid additive content, and most preferably contain only the elements C, H, O, N, P, and Cl or Br, and optionally S.

These and other embodiments and features of this invention will become still further apparent from the ensuing description and appended claims.

FURTHER DETAILED DESCRIPTION OF THE INVENTION

So far as is presently known, no compound of this invention as depicted above in Formula (I) has ever been reported heretofore.

Although there are several different ways by which the compounds of this invention can be prepared, the best method involves alkylating an appropriate N,N'-bis(ω-hydroxyalkyl)halide diamine with an appropriate alkylene dihalide to form an N,N'-alkylenebis(alkyliminoalkanol), and reacting the resultant bridged alkyliminoalkanol with aethylene oxide in the presence of a basic catalyst. The following examples illustrate the preparation of the compounds of this invention by this method.

EXAMPLE 1

Synthesis of N,N'-Bis(2-Hydroxyethyl) hexamethylenediamine

This procedure is a slight modification of that reported by L. Vargha et al. *J. Chem. Soc.* 1957, 805. A 250 mL 3-neck flask was equipped with a 60-mL constant pressure dropping funnel, a mechanical stirrer and a Claisen head fitted with a Teflon-coated thermocouple and a reflux condenser connected to a static nitrogen system. Under a static nitrogen atmosphere, stirred ethanolamine (100 mL; 1.66 mol) was heated to 125° C. with a heating mantle controlled by a J-Kem Model 250 temperature controller. Neat 1,6-dichlorohexane (40.0 g; 0.258 mol) was added dropwise over a period of 35 minutes. The reaction exotherm was controlled at 120°–130° C. by periodically dropping the heating mantle. However, several temperature excursions to 135° C. occurred. After the addition, the orange solution was heated to 155° C. under a static nitrogen atmosphere for 6 hours. After cooling overnight to ambient temperature under static nitrogen atmosphere, the orange viscous solution was diluted with sodium hydroxide (25 g; 0.625 mol) in 500 mL methanol. This yellow slurry was placed in a refrigerator for 4 hours. The slurry was suction filtered to remove the NaCl. The yellow filtrate was concentrated on a rotary evaporator under vacuum to remove the methanol at 40° C. The resulting viscous oil containing some precipitated solids was distilled under vacuum in a simple, straight takeoff distillation to remove ethanolamine at 71°–73° C. @ 9–11 mm Hg vacuum; 78.05 g (77% recovery). The pot residue, an orange glass, was then distilled in a Kugelrohr apparatus at 90°–100° C. and 0.12 torr to remove the last traces of ethanolamine. The orange viscous oil was then Kugelrohr distilled at 140°–178° C. at 0.2 torr to give a pale yellow solid; 18.6 g. This material was recrystallized from 150 mL ethyl acetate to give N,N'-bis(2-hydroxyethyl) hexamethylenediamine as white needles, which were dried in the vacuum oven at ambient temperature for 3 hours; 17.15 g (32.5% yield). mp=75°–79° C. Reported mp=78°–80° C. Proton NMR (CDCl$_3$ δ 1.4 (m,8H), 2.2 (s,4H), 3.7 (2 overlapping triplets, 5 Hz, 8H), 3.6 (t, 5 Hz, 4H); Carbon NMR (CDCl$_3$) δ 27.1, 30.1, 49.4, 51.2, 61.0.

EXAMPLE 2

N,N'-Bis(Hexadecyl) -N,N'-Bis(2-Hydroxyethyl) hexamethylenediamine

A magnetically stirred mixture of 1-bromohexadecane (7.6 g; 25 mmol), N,N'-bis(2-hydroxyethyl) hexamethylenediamine formed as in Example 1 (2.05 g; 10 mmol) and sodium carbonate monohydrate (3.7 g; 30 mmol) in 10 mL water was heated at reflux. After 18.5 hours of heating, the two phase mixture was allowed to cool to room temperature. The solidified organic layer was diluted with more water and broken up with a spatula. Suction filtration and washing with copious amounts of water gave an off-white waxy solid; 11.4 g. The off-white solid was slurried in 200 mL ether and suction filtered to yield a white amorphous solid; 2.2 g. This solid, which was insoluble in CHCl$_3$, water and DMSO, was not characterized further. The ether filtrate was concentrated in vacuo to give a pale yellow oil that slowly solidified upon standing; 6.65 g. Kugelrohr distillation at 190° C. and 0.15 torr removed a small amount of a white waxy solid (0.7 g), which was assumed to be cetyl alcohol based on GLC analysis. The pot residue from the Kugelrohr distillation solidified upon standing to give N,N'-bis(hexadecyl)-N,N'-bis(2-hydroxyethyl) hexamethylenediamine as a beige waxy solid; 5.45 g (83.5% yield). mp=29°–30° C. Reverse phase TLC (75:22:3 CHCl$_3$:MeOH:H$_2$O containing 1 vol % triethylamine) gave a single sharp spot at R$_f$ 0.46 on Whatman reverse phase MKC$_{18}$F. HPLC Analysis on C$_{18}$ column using 90:10:1 chloroform: methanol:triethylamine gave a single sharp peak at 3.14 minutes. Proton NMR (CDCl$_3$) δ 1.2 (t,6+H), 1.7 (broad s, 64+H), 3.3 (overlapping triplets, 7 Hz, 12H), 4.0 (broad s, exchangeable with D$_2$O, 2H), 5.7 (t, 7 Hz, 4H). Carbon NMR (CDCl$_3$) δ 13.9, 22.6, 27.2, 27.4, 29.3, 29.6, 31.9, 54.0, 55.8, 58.5. As a result of high integration of the aliphatic region of the proton NMR, high field proton and carbon NMR spectra were taken. These spectra showed some trace impurities, undetected in the low field spectra. The proton integration for the aliphatic region for the 300 MHz proton spectrum was slightly high, but better than the low field spectrum. IR (KBr) 3385 (broad), 2920, 2851, 1468, 1374, 1052, 722. Anal. Calcd for C$_{42}$H$_{88}$N$_2$O$_2$:C, 77.2; H, 13.6; N, 4.3; H$_2$Om 0.0. Found: C, 77.5; H, 13.3; N, 3.9; H$_2$O, 0.2. Found$^7$: C, 77.7; H, 13.6; N, 3.9.

EXAMPLE 3

N,N'-Bis(Hexadecyl)hexamethylenediamine-N,N'-Bis(Polyethoxylate)$_6$

N,N'-bis(hexadecyl)-N,N'-bis(2-hydroxyethyl) hexamethylenediamine formed as in Example 2 (4.01 g, 0.006 mol) was added to a 300 mL 316 SS Parr® reactor (Model No. 4561) and transferred with all the following necessary reagents and autoclave hardware into a dry box purged with nitrogen. Anhydrous tetrahydrofuran (THF)(70 mL) was added to the reaction cylinder via a syringe. The reaction cylinder was stirred until the N,N'-bis(hexadecyl)-N,N'-bis(2-hydroxyethyl)hexamethylenediamine was dissolved. Sodium hydride (0.30 g, 0.13 mol) was added to the reaction solution to form the alkoxide and the mixture was stirred until the hydrogen evolution subsided. The bomb head-assembly was securely tightened and removed from the dry box. The reactor was transferred to a dry ice bath, cooled to −45° C. and ethylene oxide (4.2 g, 0.095 mol) was condensed into the reactor. The valves were then closed and the reactor was warmed to room temperature and ultimately to 65° C. while it was stirred at 160 rpm. The temperature was controlled during the first 1.5 hours of initial heatup by increasing the set point of the LOVE® temperature controller in 5° C. increments. The reaction was allowed to proceed overnight using the controller to maintain the temperature at 65° C. After 12 hours, the reactor was allowed to cool to room temperature, vented and disassembled. The contents were poured out into a 500 mL round bottom flask. The reactor was rinsed with approximately 20 mL of additional THF and the combined THF solutions were treated with approximately 3 mL 1.2N HCl, stirred for 10 minutes, and concentrated in vacuo. The resulting waxy solid was resuspended in 100 mL CHCl$_3$, transferred to a 1 L separatory funnel and shaken vigorously with 30 mL of saturated sodium chloride and 30 mL of deionized water. The aqueous layer was extracted twice with 50 mL of CHCl$_3$. The combined chloroform layers were dried with MgSO$_4$, filtered and concentrated in vacuo to afford 8.0 g of amber oil. The amber oil contained an average of 6 ethyleneoxy (EO) groups on each nitrogen as determined by proton integration. This polyethoxylated amber oil was further subjected to additional pegylation.

EXAMPLE 4

N,N'-Bis(hexadecyl)hexamethylenediamine-N,N'-Bis(polyethoxylate)$_{11.5}$

N,N'-Bis(hexadecyl)hexamethylenediamine-N,N'-bis (polyethoxylate)$_6$ formed as in Example 3 (5.0 g, 4.2 mmol) was added to a 300 mL 316 SS Parr® reactor (Model No. 45611) and then it was transferred with all the necessary reagents and autoclave hardware into a dry box purged with nitrogen. Anhydrous THF (70 mL) was added to the reaction cylinder via a syringe. The reaction cylinder was stirred until the polyethoxylated amber oil was dissolved. Sodium hydride (0.22 g, 8.5 mmol) was added to the reaction solution to form the alkoxide and the mixture was stirred until the hydrogen evolution subsided. The bomb head-assembly was securely tightened and the sealed autoclave removed form the dry box. The reactor was transferred to a dry ice bath, cooled to −45° C. and ethylene oxide (3.2 g 0.073 mol) was condensed into the reactor. The valves were then closed and the reactor was warmed to room temperature and ultimately to 65° C. while it was stirred at 160 rpm. The temperature was controlled during the first 1.5 hours of initial heat up by increasing the set point of the LOVE® controller in 5° C. increments. The reaction was allowed to proceed overnight using the controller to maintain the temperature at 65° C. After 12 hours, the reactor was allowed to cool to room temperature, vented and disassembled. The contents were poured out into a 500 mL round bottom flask. The reactor was rinsed with approximately 20 mL of additional THF and the combined THF solutions were treated with approximately 3 mL 1.2N HCl, stirred for 10 minutes, and concentrated in vacuo. The resulting waxy solid was resuspended in 100 mL $CHCl_3$, transferred to a 1 L separatory funnel and shaken vigorously with 100 mL saturated sodium chloride and 50 mL deionized water. The aqueous layer was extracted twice with 50 mL $CHCl_3$. The combined chloroform layers were dried with $MgSO_4$, filtered and concentrated in vacuo to afford 7.3 g of a waxy solid. The waxy solid was then subjected to flash column chromatography using 140 g silica gel (100–200 mesh) and eluted with 80:20:1, $CHCl_3$:MeOH:$H_2O$. The solvent was stripped off by rotary evaporation to afford 5.5 g (78.6%) of N,N'-bis (hexadecyl)hexamethylenediamine-N,N'-bis (polyethoxylate) having an average of about 11.5 EO groups per molecule, as a waxy amber solid. TLC [solvent ratio 80:20:1 $CHCl_3$:MeOH:$H_2O$]$R_f$=0.62. $^1H$ NMR (90 MHz, $CDCl_3$) δ 3.63 (s, 96H), 2.7–2.5 (m, 12H), 1.24 (s, 64H), 0.86 (t, 6H); $^{13}C$ NMR (23 MHz, $CDCl_3$) δ 72.4, 70.5, 70.3, 69.3, 61.6, 54.6, 31.8, 29.5, 29.2, 27.3, 22.5, 13.9. Anal. Calcd for $C_{88}H_{180}N_2O_{25}$:C,63.43; H, 10.89; N, 1.69. Found: C, 63.17; H, 10.75; N, 1.35.

EXAMPLE 5

N,N'-Bis[(2-Hexyl)decyl)]-N,N'-Bis(2-Hydroxyethyl)hexamethylenediamine

A magnetically stirred mixture of N,N'-bis(2-hydroxyethyl)hexamethylenediamine prepared as in Example 1 (2.05 g; 10 mmol), potassium iodide (2.15 g; 12.7 mmol), anhydrous potassium carbonate (4.25 g; 30.8 mmol) and 2-(hexyl)decyl bromide (7.6 g; 25 mmol) in 15 mL reagent grade N,N-dimethylacetamide (DMAA) was slowly heated to 100°–115° C. under a static nitrogen atmosphere using a Therm-O-Watch controller. Offgassing of $CO_2$ was evident and continued for at least 1.5 hrs. After heating for 100°–115° C. for 5 hours, GC analysis of an aliquot indicated essentially complete consumption of alkyl bromide. After cooling to ambient temperature, the light orange reaction mixture was partitioned between water (100 mL) and chloroform (50 mL). The layers were separated and the aqueous phase was extracted again with chloroform (50 mL). The combined chloroform layers were washed with water (3×50 mL). The dried chloroform layer ($Na_2SO_4$) was concentrated in vacuo with a water aspirator and then with a vacuum pump at 60° C. to remove the N,N-dimethylacetamide to afford a viscous, amber oil; 7.9 g. This oil was distilled in a Kugelrohr distillation apparatus at a maximum temperature of 165° C. at 0.08 torr to remove the $C_{16}$ fraction, which mainly distilled at 100°–110° C.; 1.1 g. Proton NMR spectrum of this pale yellow oil showed that it was mainly the terminal olefin with some trace DMAA. Proton and carbon NMR spectrum of the residual viscous, amber oil in the Kugelrohr pot (6.35 g) was consistent with pure N,N'-bis[(2-hexyl)decyl)]-N,N'-bis(2-hydroxyethyl) hexamethylenediamine with no detectable monoalkylated product. In contrast, reverse phase TLC and HPLC showed trace monoalkylated product. In particular, the $R_f$ values for the N,N'-dialkylated and N-monoalkylated products on reverse phase TLC using 75:22:3 chloroform:methanol:water containing 1 vol % of triethylamine were 0.8 and 0.4 respectively.

A trace impurity with an $R_f$ value of 0.5 was also apparent in the product. Reverse phase HPLC using 80:20:1 chloroform:methanol:triethylamine showed two peaks. The major peak with a retention of 3.05 minutes was assigned to the N,N'-dialkylated product, while the minor peak at 3.65 minutes was indicative of the N-monoalkylated product. Kugelrohr distillation of this crude product at 195°–212° C. and 0.06 torr for 1 hour gave the N-monoalkyated product as a pale yellow distillate; 0.45 g (10.5% yield). The kugelrohr distillation pot contained a viscous, amber oil; 5.65 g (86.5% yield). Reverse phase HPLC and TLC analysis of this oil showed no detectable N-monoalkylated product. TLC of this oil indicated possibly some decomposition of the N,N'-dialkylated product as evident by the poorly resolved spot for the N,N'-dialkylated product. However, the proton and carbon NMR spectra showed no evidence of decomposition and the spectra were consistent with N,N'-bis[(2-hexyl)decyl)]-N,N'-bis(2-hydroxyethyl)-hexamethylenediamine. Proton NMR ($CHCl_3$) δ 0.9 (t, 4Hz, 12H), 1.25 (broad s, 58H), 2.25 (d, 5 Hz, 4H), 2.45 (overlapping triplets, 8H), 2.75 (broad s, 2H), 3.5 (t, 5 Hz, 4H). Carbon NMR ($CDCl_3$) δ 14.0 (2C), 22.6 (2C), 26.6 (2C), 27.0, 27.5, 29.3, 29.6, 29.8, 30.1, 31.9 (2C), 32.3 (2C), 36.2, 54.6, 56.4, 58.7, 59.5. IR (KBr) 3444, 2924, 2853, 1464, 1052 $cm^{-1}$. Anal. (of an earlier preparation) Calcd for $C_{42}H_{88}N_2O_2$: C, 77.2; H, 13.6; N, 4.3. Found C, 76.9; H, 13.8; N, 4.7.

EXAMPLE 6

N,N'-Bis[(2-hexyl)decyl)]-hexamethylenediamine-N,N'-Bis(polyethoxylate)$_{17.5}$ N,N'-bis[(2-hexyl)decyl)]-N,N'-bis(2-hydroxyethyl) hexamethylenediamine prepared as in Example 5 (4.00 g, 0.006 mol) was added to a 300 mL 316 SS Parr® reactor (Model No. 461) and then it was transferred with all of the following necessary reagents and autoclave hardware into a dry box purged with nitrogen. Anhydrous THF (70 mL) was added to the reaction cylinder via a syringe. Sodium hydride was added to the reaction solution to form the alkoxide and the mixture was stirred until the hydrogen evolution subsided. The bomb head-assembly was securely tightened and the sealed autoclave was removed from the dry box. The reactor was transferred to a dry ice bath, cooled to 45° C. and ethylene oxide (10.7 g, 0.24 mol) was condensed into the reactor. The valves were then closed and the reactor was warmed to room temperature and ultimately to 65° C. while it was stirred at 160 rpm. The temperature was controlled during the first 1.5 hours of initial heat up by increasing the set point of the LOVE® temperature controller in 5° C. increments. The reaction was allowed to proceed overnight using the controller to maintain the temperature at 65° C. After 12 hours, the reactor was allowed to cool to room temperature, vented and disassembled. The contents were poured out into a 500 mL round bottom flask. The reactor was rinsed with approximately 20 mL of additional THF and the combined THF solutions were treated with approximately 3 mL 1.2N HCl, stirred for 10 minutes, and concentrated in vacuo. The resulting waxy solid was resuspended in 100 mL $CHCl_3$, transferred to a 1 L separatory funnel and shaken vigorously with 100 mL of saturated sodium chloride and 50 mL of deionized water. The aqueous layer was extracted twice with 50 mL of $CHCl_3$. The combined chloroform layers were dried with magnesium sulfate, filtered and concentrated in vacuo to afford 11.26 g (85.5%) of a waxy amber solid. The waxy solid (8 g) was then subjected to flash column chromatography using 100 g silica gel (100–200 mesh) and eluted with 80:20:1, $CHCl_3$:MeOH:$H_2O$. The solvent was stripped off by rotary evaporation to afford 7.70 g of a waxy amber solid (96.2% recovery). TLC [solvent ratio 80:20:1, $CHCl_3$:MeOH:$H_2O$] Rf=0.68. $^1H$ NMR (90 MHz, $CDCl_3$) δ 3.62(s,143H), 2.60–2.26(m, 12H), 1.23(s,58H), 0.86(t,12H). $^{13}C$ NMR (23 MHz, $CDCl_3$)δ 72.4, 70.5, 70.3, 61.6, 60.0, 55.4, 54.0, 38.2, 32.1, 31.7, 30.0, 29.7, 29.5, 29.1, 26.5, 22.5, 13.9. Anal.

Calcd for $C_{112}H_{228}N_2O_{37}$ (n=17.5): C, 61.29; H, 10.47; N, 1.28. Anal. calcd for $C_{132}H_{268}N_2O_{37}$ (n=27.5): C, 60.16; H, 10.25; N, 1.06. Found: C, 60.22, H, 9.42; N, 1.30. The proton NMR spectrum integrated for 17.5 EO groups on each nitrogen. However, elemental analysis suggested that the polyoxyethylene polymer chains may be longer.

In accordance with one of its embodiments this invention provides a method of controlling pests such as insects, larvae, mites, microbes, fungi, yeasts, bacteria, weeds, etc., by contacting the pest with a pesticidal composition formed by intimately mixing together at least the following ingredients: (a) an effective pesticidal amount of at least one pesticide, (b) at least one compound of Formula (I) above, and optionally but preferably, (c) at least one carrier, solvent or diluent therefor.

Another embodiment of this invention is a pesticide composition in the form of a paste, a powder or dust, or a liquid formed by mixing together at least ingredients (a), (b) and optionally but preferably, (c) above. These compositions include (i) compositions in the form of concentrates suitable for shipment, storage, and dilution with additional carrier, diluent or solvent just before application to or contacting with the particular pest(s) for which the composition is intended, and (ii) a more dilute pesticide composition in the form of paste, granules, powder or dust, or a liquid containing an effective pesticidal amount of the composition which is adapted without modification for application to or contacting with the pest(s) which the composition is intended to control.

Representative pesticides with which the compounds of this invention may be used include the following:

Fungicides and Bactericides

Carbamate fungicides such as 3,3'-ethylenebis (tetrahydro-4,6-dimethyl-2H-1,3,5-thiadiazine-2-thione), zinc or manganese ethylenebis(dithiocarbamate), bis (dimethyldithiocarbamoyl)disulfide, zinc propylenebis (dithiocarbamate), bis(dimethyldithiocarbamoyl) ethylenediamine; nickel dimethyldithiocarbamate, methyl-1 (butylcarbamoyl)-2-benzimidazolecarbamate, 1,2-bis(3-methoxycarbonyl-2-thioureido)benzene, 1-iso-propyl-carbamoyl-3-(3,5-dichlorophenyl)hydrate, potassium N-hydroxymethyl-N-methyldithiocarbamate and 5-methyl-10-butoxycarbonylamino-10,11-dihydrodibenzo(b,f) azepine; pyridine fungicides such as zinc bis(2-hydroxy-2-(1H)pyridinethionate) and 2-pyridinethiol-1-oxide sodium salt; phosphorus fungicides such as O,O-diisopropyl S-benzylphosphorothioate and O-ethyl S,S-diphenyldithiophosphate; phthalhmide fungicides such as N-(2,6-p-diethylphenyl)phthalimide and N-(2,6-diethylphenyl)-4-methylphthalimide; dicarboxyimide fungicides such as N-trichloromethylthio-4-cyclohexene-1,2-dicarboxyimide and N-tetrachloroethylthio-4-cyclohexene-1,2-dicarboxyimide; oxathine fungicides such as 5,6-dihydro-2-methyl-21,4-oxathine-3-carboxanilido-4,4-dioxide and 5,6-dihydro-2-methyl-1,4-oxathine-3-carboxanilide;naphthoquinone fungicides such as 2,3-dichloro-1,4-naphthoquinone, 2-oxy-3-chloro-1,4-naphthoquinone copper sulfate; pentachloronitro-benzene; 1,4-dichloro-2,5-direthoxybenzene; 5-methyl-s-triazol(3,4-b)benzthiazole; 2-(thio-cyanomethylthio)benzothiazole; 3-hydroxy-5-methylisooxazole; N-2,3-dichloro-phenyltetrachlorophthalamic acid; 5-ethoxy-3-trichloromethyl-1,2,4-thiadiazole; 2,4-dichloro-6-(O-chloroanilino)-1,2,5-triazine; 2,3-dicyano-1,4-dithioanthraquinone; copper 8-quinolinate; polyoxine; validamycine; cycloheximide; sodium methanearsonate; diisopropyl 1,3-dithiolane-2-iridene malonate; 3-allyloxy-1,2-benzisothiazol-1,1-dioxide; kasugamycin; Blasticidin S; 4,5,6,7-tetrachlorophthalide; 3-(3,5-dichlorophenyl) 5-ethenyl-5-methyloxazolizine-2,4-dione; N-3,5-dichlorophenyl)-1,2-dimethylcyclopropane-1,2-dicarboxyimide; S-n-butyl-5'-para-t-butyl-benzyl-N-3-pyridyldithiocarbonylimidate; 4-chlorophenoxy-3,3-dimethyl-1-(1H,1,3,4-triazol-1-yl)-2-butanone; methyl-D, L-N-(2,6-diiethylphenyl)N-(N'-methoxyacetyl)alaninate; N-propyl-N-(2-(2,4,6-trichlorophenoxy) ethylimnidazol-1-carboxamnide; N-3,5-dichlorophenyl succinamide; tetrachloroisophthalonitrile; 2-dimethylamino-4-methyl-5-n-butyl-6-hydroxypyrimidine; 2,6-dichloro-4-nitroaniline; 3-methyl-4-chlorobenzthaol-2-one; 1,2,5,6-tetrahydro-4H-pyrrolol-[3,2,1-ij]quinoline-2-one; 3'-iso-propoxy-2-methylbenzanilide; 1-[2-(2,4-dichlorophenyl)-4-ethyl-1-3-dioxorane-2-ylmethyl)hyl]-1H, 1,2,4-triazol; 1,2-benzisothiazoline-3-one; basic copper chloride; basic copper sulfate; N'-dichlorofluoromethylthio-N,N-dimethyl-N-phenyl sulfamide; ethyl-N-(3-dimethyl-aminopropyl) thiocarbamate hydrochloride; piomycin; S,S-6-methyl-quinoxaline-2,3-diyldithiocarbonate; complex of zinc and maneb; di-zinc bis(dimethyldithio-carbamate)ethylenebis (dithiocarbamate).

Plant Growth Regulants and Herbicides

Isourea plant growth regulators such as N-methoxycarbonyl-N'-methylphenylcarbamoylethylisourea and 1-(4-chlorophenylcarbamoyl)-3-ethoxycarbonyl-2-methylisourea; other type of plant growth regulators such as sodium naphthaleneacetate, 1,2-dihydropyridazine-3,6-dione and gibberellins; triazine herbicides such as 2-methylthio-4,6-bisethylamino-1,3,5-triazine, 2-chloro-4, 6-bisethylamino-1,3,5-triazine, 2-methoxy-4-ethylamino-6-isopropylamino-1,3,5-triazine, 2-chloro-4-ethylamino-6-isopropylamino-S-triazine, 2-methylthio-4,6-bis (isopropylamino)-S-triazine and 2-methylthio-4-ethylamino-6-isopropylamino-s-triazine; phenoxy herbicides such as 2,4-dichlorophenoxyacetic acid and methyl, ethyl, and butyl esters thereof, 2-chloro-4-methylphenoxyacetic acid, 4-chloro-2-methylphenoxyacetic acid and ethyl 2-methyl-4-chlorophenoxybutylate; diphenylether herbicides such as 2,4,6-trichlorophenyl-4'-nitrophenylether, 2,4-dichlorophenyl-4'-nitrophenylether and 3,5-dimethylphenyl-4'-nitrophenylether; urea herbicides such as 3-(3,4-dichlorophenyl)-1-methoxy-1-methyl urea, 3-(3,4-dichlorophenyl)-1,1-dimethylurea and 3-(4-chlorophenyl)-1,1-dimethyl urea; carbamate herbicides such as 3-methoxycarbonylaminophenyl-N-(3-methylphenyl) carbamate, isopropyl-N-(3-chlorophenyl)carbamate and methyl-N-(3,4'-dichlorophenyl)carbamate; uracil herbicides such as 5-bromo-3-sec-butyl-6-methyluracil and 1-cyclohexyl-3,5-propyleneuracil; thiocarbamate herbicides such as S-(4-chlorobenzyl)-N,N-diethylthiocarbamate, S-ethyl-N-cyclohexyl-N-ethylthiocarbamate and S-ethylhexahydro-1H-azepine-1-carbothioate and S-ethyl-N,N-di-n-propylthiocarbamate; pyridinium herbicides such as 1,1'-di-methyl-4,4'-bispyridinium dichloride; phosphonate herbicides such as N-(phosphonomethyl)glycine; aniline herbicides such as alpha, alpha, alpha-trifluoro-2,6-dinitro-N,N-dipropyl-p-toluidine and 4-(methylsulfonyl)-2, 6-dinitro-N,N-dipropylaniline; acid anilide herbicides such as 2-chloro-2',6'-diethyl-N-(butoxymethyl)acetanilide, 2-chloro-2',6'-diethyl-N-(methoxymethyl)acetanilide, and 3,4-dichloropropioanilide; pyrazole herbicides such as 1,3-dimethyl-4-(2,4-dichlorobenzoyl)-5-hydroxypyrazole and 1,3-dimethyl-4-(2,4-dichlorobenzoyl)-5-(p-toluenesulfonyloxy)pyrazole; 5-tertbutyl-3-(2,4-dichloro-5-isopropoxyphenyl)-1,3,4-oxadiazoline-2-one;2[N-isopropyl,N-(4-chlorophenyl)carbamoyl)]-4-chloro-methyl-4-isooxazoline-3-one; 3-isopropylbenzo-2-thio-1,3-diazinone-(4-2,4-dioxide) and 3-(2-methylphenoxy) pyridazine.

Insecticides

Organophosphorus insecticides such as O,O-diethyl O-(2-isopropyl-4-methyl-6-pyrimidinyl)phosphorothioate, O,O-diethyl S-2-[(ethylthio)ethyl]phosphorodithioate,O,O-dimethyl)-(3-methyl-4-nitrophenyl)thiophosphate, O,O-dimethyl S-(N-methylcarbamoyl-methyl)-phosphorodithioate, O,O-dimethyl S-(N-methyl-N-formylcarbamoylmethyl)-phosphorothioate, O,O-dimethyl S-2-[(ethylthio)ethyl]phosphorodithioate,O,O-diethyl S-2diethyl S-2-[(ethylthio)-ethyl] phosphorodithioate, O,O-dimethyl-1-hydroxy-2,2,2-trichloroethylphosphonate, O,O-diethyl-O-(5-phenyl-3-isooxyazolyl)phosphorothioate, O,O-dimethyl O-(2,5-dichloro-4-bromophenyl)phosphorothioate, O,O-dimethyl O-(3-methyl-4-methylmercaptophenyl)thiophosphate, O-ethyl O-p-cyanophenyl phenylphosphorothioate, O,O-dimethyl-S-(1,2-dicarboethoxyethyl)-phosphorodithioate, 2-chloro-(2,4,5-trichlorophenyl)vinyldimethylphosphate, 2-chloro-1-(2,4-dichlorophenyl)vinyl dimethyl phosphate, O,O-dimethyl O-p-cyanophenyl phosphorothioate, 2,2-dichlorovinyl dimethyl phosphate, O,O-diethyl O-2,4-dichlorophenyl phosphorothioate, ethyl mercaptophenylacetate O,O-dimethyl phosphorodithioate, S-[(6-chloro-2-oxo-3-benzooxy-azolinyl)methyl]-O,O-diethyl phosphorodithioate, 2-chloro-(2,4-dichlorophenyl)vinyl diethylphosphate O,O-diethyl O-(3-oxo-2-phenyl-2H-pyridazine-6-yl)phosphorothioate, O,O-dimethyl S-(1-methyl-2-ethylsulfinyl)-ethyl phosphorothioate, O,O-dimethyl S-phthalimidomethyl phosphorodithioate, O,O-diethyl 2,2,2-trichloroethanol, 2-(p-tert-butylphenoxy) isopropyl-2'-chloroethylsulfite, azooxybenzene,di-(p-chlorophenyl)-cyclopropyl carbinol, di[tri(2,2-dimethyl-2-phenylethyl)tin]oxide, 1-(4-chlorophenyl)-3-(2,6-difluorobenzoyl)urea and S-tricyclohexyltin O,O-diisopropylphosphorodithioate.

Insect Repellents

The following insect repellents may be employed herein: 2-ethyl-1,3-hexanediol; N-octyl bicycloheptene dicarboximiide; N,N-diethyl-M-toluamide; 2,3,4,5-Bis(2-butylene) tetrahydro-2-furaldehyde; di-n-propyl isocinchomeronate; and 2-hydroxyethyl-n-octyl sulfide.

The liquid media for the solutions and suspensions preferably are predominately if not substantially entirely composed of water, and when in the form of concentrates for subsequent dilution on site before use, the liquid medium for such solutions or suspensions is preferably deionized water.

When in the form of granules, powders or dusts, the mixture may contain finely-divided solid diluents or carriers such as talc, gypsum, Fuller's earth, kaolin, kieselguhr, bentonite, dolomite, calcium carbonate, and powdered magnesia. They may also be formulated as dispersible powders, extruded granules, or grains, and in this case it is desirable to include a wetting agent to facilitate the dispersion of powder, granules, or grains in the liquid carrier. Additionally, formulations in the form of powders can be applied to vegetation as foliar dusts.

The weight ratio of the pesticide ingredient(s) to compound(s) of this invention will typically be in the range of about 10:1 to 1:2, and preferably in the range of about 5:1 to about 1:1. On the basis of the teachings herein, departures from these ranges are permissible and within the purview of this invention, whenever such departures are deemed necessary or desirable in any given situation. As regards the proportions of the pesticide ingredient(s) plus compound(s) of this invention in compositions for use or sale, the amount can vary from as little as a fraction of 1% up to 100% depending upon the particular ingredients being used, the application for which the composition is intended, and the type of composition (i.e., whether it is a concentrate for sale for dilution at the site of application or whether it is the composition to be contacted with the particular type of pest(s) to be controlled or the locus or habitat thereof. Naturally, in the latter case the amount of the pesticide ingredient(s) plus compound(s) of this invention will be an amount that is at least sufficient to effectively combat the particular pest(s) in question.

Herbicides and plant growth regulants are a preferred type of pesticides and of these, compositions based on glyphosate salts as the principal or sole herbicide and/or plant growth regulant are especially preferred. Thus, in another of its embodiments, this invention provides a method of controlling vegetation by applying to plant foliage as a foliar dust or as granules, or preferably, as a spray, a herbicidal or plant growth regulant composition formed by mixing together at least the following ingredients: (a) an effective herbicidal or plant growth regulant amount of at least one herbicide or plant growth regulant, including pre-emergent and post-emergent types, and most preferably an agriculturally acceptable salt of glyphosate, such as an amine, ammonium, alkali metal, alkylsulfonium, alkylphosphonium, sulfonylamine, and/or aminoguanidine salt of glyphosate, (b) at least one compound of Formula (I) above, and optionally but preferably, (c) at least one carrier, solvent or diluent therefor. When using a glyphosate salt as ingredient (a), such herbicidal or plant growth regulant composition is preferably in the form of an aqueous solution or suspension which is applied to the plant foliage by spraying. The solutions used for these operations are preferably, but not necessarily, polyvalent metal-free solutions.

Another embodiment of this invention is a herbicidal or plant growth regulant composition of the pre-emergent or post-emergent type in the form of granules, powder or dust, or a liquid, which composition is formed by mixing together at least ingredients (a), (b) and optionally but preferably (c), each as described in the immediately preceding paragraph. These compositions include (i) compositions in the form of concentrates suitable for shipment, storage, and dilution with additional carrier, diluent or solvent just before application to the particular foliage or land site for which the composition is intended, and (ii) a more dilute herbicidal or plant growth regulant composition in the form of paste, granules, suspension, powder or dust, or solution containing an effective herbicidal and/or plant growth regulant amount of the composition which is adapted without modification for application to the plant foliage to be controlled, or to the land site where the desired control is to occur. Optionally, one or more other suitably compatible ingredients such as secondary herbicides or plant growth regulants, secondary surfactants, dyes, humectants, corrosion inhibitors, stickers, spreaders and thickeners, can be included as ingredients in these herbicidal and plant growth regulant compositions. Such herbicidal and/or growth regulant compositions can be formed in various ways, such as, for example, by evaporating to dryness (e.g., by spray drying, extrusion or pan granulation) a solution of components (a) and (b) above, and optionally (c) above.

The herbicidal (phytotoxic) and the plant growth regulant compositions of this invention include aqueous concentrates which can be shipped and stored until diluted with more water on site to produce the final solution for application to the foliage as by spraying. Likewise the herbicidal and the plant growth regulant compositions of this invention include the more dilute aqueous solutions for use in application to the foliage. These more dilute aqueous solutions are preferably formed simply by suitably diluting an aqueous concentrate of this invention with water (if a powder or granular concentrate) or with more water (if a liquid concentrate) to achieve the appropriate herbicidal or plant regulant dosage, but alternatively, can be formed on site by intimately mixing the separate ingredients or sub-combinations thereof with sufficient water on site to achieve the appropriate dosage. Use of the solid or liquid concentrates of this invention is preferable as it is a much simpler operation and minimizes the possibility of blending errors. Moreover, if desired, other components such as fertilizers, penetrants, spreaders, stickers, etc., can be introduced into the final solution at the time the concentrate is blended with water to form the diluted solution for application to the foliage.

It will be appreciated that to effect control of undesired plant vegetation pursuant to this invention, recourse may be had to herbicidal activity whereby undesired vegetation is killed and/or to plant growth regulant activity whereby the further growth of the vegetation is stunted, inhibited and/or slowed without actually killing all of the undesired vegetation treated with the composition.

FURTHER DESCRIPTION OF PREFERRED EMBODIMENTS OF THE INVENTION

In connection with the preferred herbicidal and/or plant growth regulant compositions based on glyphosate and the use of such compositions, the following additional details may be of interest.

For descriptions of the identities and methods for the preparation of the glyphosate ingredients one may find ample descriptions in the literature. See for example, U.S. Pat. No. 3,799,758 to J. E. Franz which describes amine salts and alkali metal salts of glyphosate, and the production of glyphosate by such methods as the phosphonomethylation of glycine, the reaction of ethyl glycinate with formaldehyde and diethylphosphite, and the oxidation of the corresponding aminophosphinic compounds. Another method involves conducting a Mannich reaction with phosphorous acid and formaldehyde on iminodiacetic acid followed by controlled oxidation to N-(phosphonomethyl)glycine. The alkylsulfonium salts of glyphosate are described for example in U.S. Pat. No. 4,315,765 to G. B. Large, and analogous procedures can be used for producing alkylphosphonium salts. Sulfonylamine and aminoguanidine salts of glyphosate which are also suitable for use pursuant to this invention are disclosed in EP-A-0 088 180. The patent literature contains numerous additional references to various other methods for the production of glyphosate. See for example U.S. Pat. Nos. 4,851,159; 4,898,972; 4,937,376; 4,952,723; 5,061,820; and 5,072,033 to Fields Jr. et al.; 5,023,369 to Fields, Jr.; 4,853,159 to Riley et. al; and 5,047,579 to Glowka et al., as well as relevant references cited in these patents. Fields, Jr. et al. U.S. Pat. No. 4,965,403 describes a process for producing the alkali metal salts of glyphosate.

Typically the amine of the glyphosate amine salts used in the practice of this invention has a molecular weight of less than 300. A preferred amine salt of glyphosate for use in this invention is a salt formed with isopropyl amine. Of the alkali metal salts of glyphosate, sodium is the preferred cation for use in this invention. Inasmuch as glyphosate has more than one replaceable hydrogen atom, either or both of mono- and dialkali metal salts of glyphosate can be formed and used. Of the alkylsulfonium and alkylphosphonium salts, the trimethylsulfonium salt of glyphosate is preferred.

Aqueous solutions of glyphosate salts devoid of other adjuvants are commercially available from Monsanto Company and these solutions are suitable for use in forming the compositions of this invention.

Formula (I) above depicts the novel compounds of this invention which can be used as adjuvants with glyphosate (as well as with the other pesticides referred to above). Chemically they can be identified as $\omega,\omega'$-[$\alpha,\omega$-alkanediylbis(alkylimino)]bis(alkanolpolyethoxylates) in which (i) the alkane group has in the range of 4 to 12 carbon atoms, (ii) the alkyl groups can be the same or different and contain up to about 24 carbon atoms each, and (iii) the number of ethyleneoxy groups in each polyethoxylate group is in the range of 2 to about 50. Of these novel compounds, various preferred sub-categories are worthy of special mention:

A) A 2,2'-[$\alpha,\omega$-alkanediylbis(alkylimino)]bis(ethanolpolyethoxylate) as above in which the alkane group has in the range of 6 to 12 carbon atoms.

B) A 2,2'-[$\alpha,\omega$-alkanediylbis(alkylimino)]bis(ethanolpolyethoxylate) as above in which each alkyl group is a primary alkyl group having in the range of about 6 to about 24 carbon atoms.

C) A 2,2'-[$\alpha,\omega$-alaanediylbis(alkylimino)]bis(ethanolpolyethoxylate) as above in which each alkyl group is a primary alkyl group having in the range of 14 to about 20 carbon atoms.

D) A 2,2'-[$\alpha,\omega$-alkanediylbis(alkylimino)]bis(ethanolpolyethoxylate) as above in which the number of ethyleneoxy groups in each polyethoxylate group is in the range of 4 to about 30.

E) A 2,2'-[$\alpha,\omega$-alkanediylbis(alkylimino)]bis(ethanolpolyethoxylate) as above in which: (a) the alkane group has in the range of 6 to 12 carbon atoms; and (b) the number of ethyleneoxy groups in each polyethoxylate group is in the range of 4 to about 30.

F) A 2,2'-[$\alpha,\omega$-alkanediylbis(alkylimino)]bis(ethanolpolyethoxylate) as in E) above in which each alkyl group is a primary alkyl group having in the range of 14 to about 20 carbon atoms.

G) A 2,2'-[$\alpha,\omega$-alkanediylbis(alkylimino)]bis(ethanolpolyethoxylate) as in F) above in which (a) the alkane group has 6 carbon atoms and (b) each alkyl group is a primary alkyl group having about 16 carbon atoms.

H) A 2,2'-[1,6-hexanediylbis(n-hexadecylimino)]bis(ethanolpolyethoxylate) in which the number of ethyleneoxy groups in each polyethoxylate group is in the range of 4 to about 30.

I) A 2,2'-[$\alpha,\omega$-alkanediylbis(alkylimino)]bis(ethanolpolyethoxylate) as above in which each alkyl group is a primary alkyl group having in the range of 4 to about 24 carbon atoms and has a branch in the 2-position.

J) A 2,2'-[$\alpha,\omega$-alkanediylbis(aliylimino)]bis(ethanolpolyethoxylate) as above in which each alkyl group is a primary alkyl group having in the range of 8 to about 24 carbon atoms and has a branch in the 2-position, and where such branch has 4 less carbon atoms than the remainder of the alkyl group.

K) A 2,2'-[1,6-hexanediylbis(2-hexyldecylimino)]bis(ethanolpolyethoxylate) in which the number of ethyleneoxy groups in each polyethoxylate group is in the range of 4 to about 30.

Table 1 sets forth general and preferred proportions for use in forming water-soluble glyphosate concentrate formulations of this invention. The percentages given in Table 1 are weight percentages, and represent weight percent of the total composition. The percentages for the glyphosate salt, such as an amine, ammonium, alkali metal, alkylsulfonium, alkylphosphonium, sulfonylamine, and/or aminoguanidine salt ("Glyphosate Salt") as given in Table 1 are on an active ingredient basis and are in terms of glyphosate acid equivalent (i.e., the weight of the particular salt-forming portion of the product is excluded from the weight of the salt). Likewise the amount of any water associated with the salt as received is excluded from consideration as regards the percentages of the Glyphosate Salt shown in the table. The novel compounds of this invention ("Adjuvant") are compounds of Formula (I) above and the percentages thereof are expressed in Table I in terms of the compound(s) in neat (undiluted) form.

TABLE 1

| Ingredient | General Range, wt % | Preferred Range, wt % |
| --- | --- | --- |
| (a) Glyphosate Salt | 0.1 to 65% | 18 to 65% |
| (b) Adjuvant | 1 to 70% | 10 to 25% |
| Inert Ingredient(s) | 0 to 20% | 0 to 5% |
| Water | Balance to 100% | Balance to 100% |

Table 2 sets forth the proportions which can be used in forming the powder or granular glyphosate compositions of this invention. As in Table 1, the percentages given in Table 2 are weight percentages on an active ingredient basis, and represent weight percent of the total composition. And as above, the percentages for glyphosate salt given in Table 2 are in terms of glyphosate acid equivalent.

TABLE 2

| Ingredient | General Range, wt % | Preferred Range, wt % |
| --- | --- | --- |
| (a) Glyphosate Salt | 10 to 99% | 75 to 98% |
| (b) Adjuvant | 1 to 90% | 2 to 25% |
| Other Ingredient(s) | 0 to 20% | 0 to 10% |

The diluted solutions for application to the plant foliage are typically formed prior to application using a tank mixer, spray tank or similar apparatus. The dosage level of the composition applied to the plant foliage will depend to some extent upon the plant species being treated, the extent of control desired, and the prevailing weather conditions. Generally speaking, however, the amount applied will be a herbicidal or growth regulant amount within the range of about 50 to about 1250 grams of glyphosate (on an acid equivalent basis, i.e., excluding the weight of the cationic salt associated therewith) per hectare. In terms of ounces avoirdupois per acre this range corresponds (on the same acid equivalent basis) to from about 0.7 to about 20 ounces of glyphosate per acre). In accordance with this invention it is preferred to employ a herbicidal or plant growth regulant amount (again on an acid equivalent basis) falling within the range of about 200 to about 830 grams of glyphosate per hectare which corresponds (on the same acid equivalent basis) to about 3 to about 12 ounces avoirdupois of glyphosate per acre), as this is generally sufficient to control most undesired plant species, is below the dosage currently recommended for herbicidal use of glyphosate formulations, and is thus more economical and environmentally friendly. On the basis of this disclosure and the new technology described herein, it is now possible to make departures from the foregoing ranges whenever such is deemed necessary or desirable in any given situation.

Herbicide performance enhancing capabilities of the adjuvants of this invention were investigated by a group of greenhouse tests in which two compounds of this invention, viz., N,N'-bis(hexadecyl)hexamethylenediamine-N,N'-bis(polyethoxylate)$_{11.5}$ ("Linear-HHDP") and N,N'-bis[(2-hexyl)decyl)]hexamethylenediamine-N,N'-bis(polyethoxylate)$_{17.5}$ ("β-Branched-HHDP") were used as performance enhancers for glyphosate in the control of morning-glory ("MG") and hemp sesbania ("HS"). The test formulations consisted of aqueous solutions made from N-(phosphonomethyl)glycine isopropyl amine salt, water, and either the Linear-HHDP or the β-Branched-HHDP. No other component or ingredient was employed in forming the test formulations.

The glyphosate used in forming these formulations was ROUND-UP® D-Pak from Monsanto, which is a 62.0% aqueous solution of the glyphosate isopropyl amine salt in water with no other component therein. The control formulation was an aqueous solution of N-(phosphonomethyl)glycine isopropyl amine salt and the commercial adjuvant INDUCE® (Helena Chemical Company) which, according to *A Guide to Agricultural Spray Adjuvants Used in the United States*, by T. L. Harvey, 1992–93 Edition, Thomson Publications, Fresno, Calif., page 33 is alkyl polyoxyalkane ether, free fatty acids and IPA, which is an adjuvant currently recommended for use in glyphosate formulations. The formulations of this invention and the control formulations were applied to the plant species at the rates of 250 and 500 grams of glyphosate acid equivalent ("a.e.") per hectare. Two sets of these solutions were used. One set was formed using adjuvant to glyphosate (acid equivalent basis) ratios of 1:2. In the other set the ratios were 1:4.

Tables 3 and 4 summarize these test results at 21 days after treatment in terms of their statistical significance within 95% confidence limits. Thus the symbol ⊙ signifies that the test formulation of this invention gave results that statistically were superior to the results given by the control. The symbol +e,crc ++ee signifies that the test formulation of this invention gave results that statistically were equivalent to results given by the control. The symbol ⊖ signifies that statistically the result was not equivalent to that of the control but nevertheless demonstrated plant growth regulant activity. The results of Table 3 relate to effectiveness as measured by dry weight (biomass) of the treated plants as compared to the dry weight of the untreated plants of the same species. Table 4 relates to effectiveness in relation to plant height of the treated plants versus plant heights of the untreated plants of the same species.

TABLE 3

Control of Morning-Glory and Hemp Sesbania Under Greenhouse Conditions

| Adjuvant | Adjuvant/ Glyphosate (a.e.) Ratio | Glyphosate Dosage Rate, grams (a.e.) per Hectare | MG Biomass, % of Untreated Plants | HS Biomass, % of Untreated Plants |
| --- | --- | --- | --- | --- |
| Linear-HHDP | 1:2 | 250 | ⊕ | ⊕ |
| β-Branched-HHDP | 1:2 | 250 | ⊕ | ⊕ |

TABLE 3-continued

Control of Morning-Glory and Hemp Sesbania Under Greenhouse Conditions

| Adjuvant | Adjuvant/ Glyphosate (a.e.) Ratio | Glyphosate Dosage Rate, grams (a.e.) per Hectare | MG Biomass, % of Untreated Plants | HS Biomass, % of Untreated Plants |
|---|---|---|---|---|
| Linear-HHDP | 1:4 | 250 | ⊙ | ⊖ |
| β-Branched-HHDP | 1:4 | 250 | ⊙ | ⊕ |
| Linear-HHDP | 1:2 | 500 | ⊕ | ⊕ |
| β-Branched-HHDP | 1:2 | 500 | ⊕ | ⊕ |
| Linear-HHDP | 1:4 | 500 | ⊕ | ⊖ |
| β-Branched-HHDP | 1:4 | 500 | ⊕ | ⊕ |

TABLE 4

Control of Morning-Glory and Hemp Sesbania Under Greenhouse Conditions

| Adjuvant | Adjuvant/ Glyphosate (a.e.) Ratio | Glyphosate Dosage Rate, grams (a.e.) per Hectare | MG Plant Height, % of Untreated Plants | HS Plant Height, % of Untreated Plants |
|---|---|---|---|---|
| Linear-HHDP | 1:2 | 250 | ⊕ | ⊕ |
| β-Branched-HHDP | 1:2 | 250 | ⊕ | ⊙ |
| Linear-HHDP | 1:4 | 250 | ⊕ | ⊕ |
| β-Branched-HHDP | 1:4 | 250 | ⊕ | ⊕ |
| Linear-HHDP | 1:2 | 500 | ⊖ | ⊖ |
| β-Branched-HHDP | 1:2 | 500 | ⊕ | ⊕ |
| Linear-HHDP | 1:4 | 500 | ⊕ | ⊖ |
| β-Branched-HHDP | 1:4 | 500 | ⊕ | ⊙ |

Using a rating scale of 1 to 3 where the higher the number the greater the injury to the plant, the above glyphosate compositions when applied to hemp sesbania at a dosage rate (a.e.) of 500 grams per hectare gave the results shown in Table 5. At the dosage rate (a.e.) of 250 grams per hectare these beneficial effects were not exhibited.

TABLE 5

Phytotoxic Effect Produced with Hemp Sesbania in Two Days after Treatment

| Adjuvant | Adjuvant/Glyphosate (a.e.) Ratio | Plant Injury Rating, Two Days after Treatment |
|---|---|---|
| Linear-HHDP | 1:2 | 2.3 |
| Linear-HHDP | 1:4 | 2.3 |
| β-Branched-HHDP | 1:2 | 2.8 |
| β-Branched-HHDP | 1:4 | 2.5 |
| Control | 1:2 | 2.3 |
| Control | 1:4 | 1.8 |

It is to be understood that chemical compounds referred to by chemical name or formula anywhere in the specification or claims hereof, whether referred to in the singular or plural, are identified as they exist prior to coming into contact with another substance referred to by chemical name or chemical type (e.g., a reactant, a solvent, a diluent, or etc.). As a result of such contacting one or more chemical changes or transformations such as solvolysis, ionization, complex formation, chemical reaction or the like, may take place, and such changes or transformations, if the result of conducting an operation or procedure in accordance with this disclosure, are within the scope and contemplation of this invention. Thus there is no requirement that any chemical compound must remain unchanged when mixed with another ingredient, substance or compound as long as the operation or procedure being used is in accordance with the plain and ordinary meaning of this specification using common sense and ordinary knowledge and skill of a person skilled in the art. Accordingly, even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients in accordance with the present disclosure. The fact that the substance, component or ingredient may have lost its original identity through a chemical reaction or transformation during the course of such contacting, blending or mixing operations is thus wholly immaterial for an accurate understanding and appreciation of this disclosure and the claims thereof.

Each and every patent or other publication referred to in any portion of this specification is fully incorporated into this disclosure by reference as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

What is claimed is:

1. A $\omega,\omega'$-[α,ω-alkanediylbis(alkylimino)]bis(alkanolpolyethoxylate) in which(i) the alkane group has in the range of 4 to 12 carbon atoms, (ii) the alkyl groups can be the same or different, and are primary alkyl groups which contain 6 to about 24 carbon atoms each, (iii) each alkanol group contains, independently, in the range of from 2 to about 6 carbon atoms, and (iv) the number of ethyleneoxy groups in each polyethoxylate group is in the range of 2 to about 50.

2. A 2,2'-[α,ω-alkanediylbis(alkylimino)]bis(ethanolpolyethoxylate) in accordance with claim 1 in which the alkane group has in the range of 6 to 12 carbon atoms.

3. A 2,2'-[α,ω-alkanediylbis(alkylimino)]bis(ethanolpolyethoxylate) in accordance with claim 1 in which each alkyl group is a primary alkyl group having in the range of 14 to about 20 carbon atoms.

4. A 2,2'-[α,ω-alkanediylbis(alkylimino)]bis(ethanolpolyethoxylate) in accordance with claim 1 in which the number of ethyleneoxy groups in each polyethoxylate group is in the range of 4 to about 30.

5. A 2,2'-[α,ω-alkanediylbis(alkylimino)]bis(ethanolpolyethoxylate) in accordance with claim 1 in which: (a) the alkane group has in the range of 6 to 12 carbon atoms; and (b) the number of ethyleneoxy groups in each polyethoxylate group is in the range of 4 to about 30.

6. A 2,2'-[α,ω-alkanediylbis(alkylimino)]bis(ethanolpolyethoxylate) in accordance with claim 5 in which each alkyl group is a primary alkyl group having in the range of 14 to about 20 carbon atoms.

7. A 2,2'-[α,ωa-alkanediylbis(alkylimino)]bis(ethanolpolyethoxylate) in accordance with claim 6 in which (a) the alkane group has 6 carbon atoms and (b) each alkyl group is a primary alkyl group having about 16 carbon atoms.

8. A 2,2'-[α,ω-alkanediylbis(alkylimino)]bis(ethanolpolyethoxylate) in accordance with claim 1, namely 2,2'-[1,6-hexanediylbis(n-hexadecylimino)]bis(ethanolpolyethoxylate)in which the number of ethyleneoxy groups in each polyethoxylate group is in the range of 4 to about 30.

9. A 2,2'-[α,ω-alkanediylbis(alkylimino)]bis(ethanolpolyethoxylate) in accordance with claim 1 in which each alkyl group is a primary alkyl group having in the range of 8 to about 24 carbon atoms and has a branch in the 2-position.

10. A 2,2'-[α,ω-alkanediylbis(alkylimino)]bis(ethanolpolyethoxylate) in accordance with claim 1 in which each alkyl group is a primary alkyl group having in the range of 8 to about 24 carbon atoms and has a branch in the 2-position, said branch having 4 less carbon atoms than the remainder of the alkyl group.

11. A 2,2'-[α,ω-alkanediylbis(alkylimino)]bis(ethanolpolyethoxylate) in accordance with claim 1, namely 2,2'-[1,6-hexanediylbis(2-hexyldecylimino)]bis(ethanolpolyethoxylate) in which the number of ethyleneoxy groups in each polyethoxylate group is in the range of 4 to about 30.

12. A pesticidal composition comprising a pesticide and at least one ω,ω'-[α,ωalkanediylbis(alkylimino)]bis(alkanolpolyethoxylate) in accordance with any one of claims 1, 2, and 3–11 taken individually.

13. A herbicidal or plant growth regulant composition comprising at least one agriculturally acceptable salt of glyphosate and at least one ω,ω'-[α,ω-alkanediylbis(alkylimino)]bis(alkanolpolyethoxylate) in accordance with any one of claims 1, 2, and 3–11 taken individually.

* * * * *